(12) United States Patent
Maloney et al.

(10) Patent No.: US 12,370,132 B2
(45) Date of Patent: Jul. 29, 2025

(54) ORAL COMPOSITIONS

(71) Applicant: Colgate-Palmolive Company, New York, NY (US)

(72) Inventors: Venda Porter Maloney, Metuchen, NJ (US); Laurence Du-Thumm, Princeton, NJ (US); Luciana Rinaudi Marron, Somerset, NJ (US); Stacey Lavender, Chesterfield, NJ (US); Vyoma Patel, Hillsborough, NJ (US); Ekta Makwana, Monroe, NJ (US); Andrei Potanin, Hillsborough, NJ (US); Baran Teoman, Union, NJ (US); Shashank Potnis, North Brunswick, NJ (US); Gayatri Sachin Patel, Edison, NJ (US); Carl Myers, Wayne, NJ (US)

(73) Assignee: Colgate-Palmolive Company, New York, NY (US)

( * ) Notice: Subject to any disclaimer, the term of this patent is extended or adjusted under 35 U.S.C. 154(b) by 34 days.

(21) Appl. No.: 17/961,785

(22) Filed: Oct. 7, 2022

(65) Prior Publication Data
US 2023/0112970 A1    Apr. 13, 2023

Related U.S. Application Data

(60) Provisional application No. 63/253,711, filed on Oct. 8, 2021.

(51) Int. Cl.
| *A61K 8/04* | (2006.01) |
| *A61K 8/44* | (2006.01) |
| *A61Q 11/00* | (2006.01) |

(52) U.S. Cl.
CPC .............. *A61K 8/042* (2013.01); *A61K 8/44* (2013.01); *A61Q 11/00* (2013.01); *A61K 2800/92* (2013.01)

(58) Field of Classification Search
CPC . A23G 3/364; A23G 3/42; A23G 3/44; A61Q 11/00; A61K 2800/92; A61K 8/042;
(Continued)

(56) References Cited

U.S. PATENT DOCUMENTS

| 2005/0074489 A1* | 4/2005 | Gonzales | ............. A61K 9/0007 424/466 |
| 2007/0116820 A1* | 5/2007 | Prakash | ................... A23L 9/12 426/548 |

(Continued)

FOREIGN PATENT DOCUMENTS

| JP | 2004-321092 | 11/2004 |
| JP | 2004321092 A * | 11/2004 |

(Continued)

OTHER PUBLICATIONS

JP2004321092 A English translation from Google Patents (Year: 2004).*

(Continued)

*Primary Examiner* — Walter E Webb
*Assistant Examiner* — Amanda Michelle Petritsch

(57) ABSTRACT

Disclosed herein are oral compositions comprising an amino acid and a gelling agent. In certain embodiments, the chewable composition is in the form of a gummy comprising arginine and pectin. Related kits and methods of use are further provided.

19 Claims, 4 Drawing Sheets

(58) Field of Classification Search
CPC ... A61K 8/44; A61K 8/65; A61K 8/73; A61K 8/0216
See application file for complete search history.

(56) References Cited

U.S. PATENT DOCUMENTS

| | | | |
|---|---|---|---|
| 2008/0286340 | A1 | 11/2008 | Sven-Borje et al. |
| 2022/0241172 | A1 | 8/2022 | Ontumi et al. |

FOREIGN PATENT DOCUMENTS

| | | | | |
|---|---|---|---|---|
| WO | 2008/140371 | | 11/2008 | |
| WO | WO-2008140371 A1 | * | 11/2008 | ............... A23G 3/44 |
| WO | 2012/023936 | | 2/2012 | |
| WO | 2021/119650 | | 6/2021 | |
| WO | 2022/266523 | | 12/2022 | |

OTHER PUBLICATIONS

Bourbon, 2020, "Sour Ume Plum Gummy", Mintel Database GNPD AN: 7831681.
Harbaland Naturals, 2021, "Blueberry Burst Gummy Snack", Mintel Database GNPD AN: 8628877.
International Search Report and the Written Opinion of the International Searching Authority issued in International Application PCT/US2022/046022 mailed Feb. 3, 2023.
Mikakuto, 2021, "Marvel Grape Flavoured Fruit Juice Gummy", Mintel Database GNPD AN: 8526147.
MacDougall, et al., "The effect of peptide-pectin interactions on the gelation behaviour of a plant cell wall pectin," Carbohydrate Research, 335(2): 115-126 (2001).
Guignon, Anne Nugent, "Arginine: A Magical Weapon in the War Against Oral Microbial Diseases," https://www.rdhmag.com/patient-care/article/16408932/arginine-and-oral-health-its-affect-on-oral-microbial-diseases, retrieved Oct. 7, 2022, pp. 1-10.

* cited by examiner

ORAL COMPOSITIONS

CROSS-REFERENCE TO RELATED APPLICATION

This application claims the benefit of priority from U.S. Provisional Application No. 63/253,711, entitled "ORAL CARE COMPOSITIONS" and filed Oct. 8, 2021, the contents of which are hereby incorporated herein in their entirety.

BACKGROUND

A wide variety of agents have been suggested in the art to inhibit or reduce plaque formation and the oral infections and dental disease associated with plaque formation. Arginine and related salts are believed to provide caries prevention benefits.

Oral hygiene may be maintained through regular brushing with toothpaste and/or rinsing with mouthwash. Regular use of such toothpastes and mouthwashes can reduce the growth of dental plaque, decrease the risk of developing gum disease, and prevent tooth decay. While these oral care products have been traditionally used, there is a market need for products that can be used on the go. However, the types of oral care products which address these needs are limited.

While consumer preference and demand for chewable oral care compositions is growing, one issue that arises, however, is that the formulation of compositions containing basic amino acids into a pectin base may lead to polymer aggregation as the basic amino acids have the potential to act as non-covalent crosslinking agents in pectin networks. In addition to their effect on crosslinking, the basic amino acids within the pectin network may have a marked effect on the swelling behavior of the gel. It is believed that this can be partly due to specific interactions of the amino acid with the pectin chain, which has the effect of reducing its effective charge. See, e.g., MacDougall A J, et al., *The Effect of Peptide-Pectin Interactions on the Gelation Behaviour of a Plant Cell Wall Pectin*, Carbohydrate Research 335 (2001) 115-126. Thus, it is conventionally believed that the incorporation of basic amino acids into a composition containing pectin may result in degradation of the pectin's ability to form pectin networks.

Accordingly, there is a need for a chewable product, such as an oral care product or edible product, that can be an alternative or supplement to products currently on the market. Additionally, there is also a need to create a stabilized chewable product (e.g., soft chew or gummy), such as an oral care composition or an edible composition, that can be efficiently manufactured in light of the formulation difficulties that may be associated with basic amino acids (e.g., arginine) and acidic gelling agents (e.g., pectin).

BRIEF SUMMARY

The present disclosure provides a chewable product, such as an oral care product or edible product, that can be an alternative or supplement to products currently on the market. Further provided is a stabilized chewable composition (e.g., soft chew or gummy), such as an oral care composition and an edible composition, that incorporates an amino acid (e.g., a basic amino acid) that can be efficiently manufactured in light of the difficulties associated with basic amino acids (e.g., arginine) and acidic gelling agents (e.g., pectin).

Without intending to be bound by a particular theory, it is hypothesized that a significant factor in the beneficial effect of arginine is that arginine and other basic amino acids can be metabolized by certain types of bacteria, e.g., *Streptococcus sanguinis* which are not cariogenic and which compete with cariogenic bacteria, such as *S. mutans*, for position on the teeth and in the oral cavity. The arginolytic bacteria can use arginine and other basic amino acids to produce ammonia, thereby raising the pH of their environment. It is believed that cariogenic bacteria metabolize sugar to produce lactic acid, which tends to lower the plaque pH and demineralize the teeth, and which ultimately leads to cavities. It is believed that regular use of a composition containing arginine, over time, will lead to a relative increase in the arginolytic bacteria and a relative decrease in the cariogenic bacteria, resulting in a higher plaque pH, which leads to tooth remineralization and caries prevention.

However, it is conventionally believed that arginine can interfere with the gelation process of acidic gelling agents, such as pectin, as arginine demonstrates a general binding affinity for acidic gelling agents. In turn, this may have the effect of blocking sites for cross-linking during gelation. The inventors have surprisingly discovered that compositions (e.g., chewable compositions, oral care compositions, and/or edible compositions) according to the present disclosure are stable and effective means for transporting arginine to the surface of the teeth in order to achieve anti-caries benefits. Additionally, the inventors discovered that certain gelling agents and amino acids in particular amounts and ratios as disclosed herein surprisingly achieve a significant increase in ability to prevent and/or reduce caries. For instance, it was unexpectedly discovered that certain embodiments of the oral care compositions may promote desirable bacteria and reduce or hinder the growth of undesirable bacteria associated with caries. Certain embodiments, for example, may reduce the amount of *S. mutans* in a biofilm in the oral cavity of an individual by about 5% or more within 8 hours of chewing the chewable composition for 45 seconds as compared to if the same individual proceeded with the same dietary and oral care plan but did not chew the chewable composition. Preferably, the amount of *S. mutans* is reduced by about 10% or more, 15% or more, or 20% or more in a biofilm in the oral cavity of an individual within 8 hours of chewing the chewable composition for 45 seconds as compared to if the same individual proceeded with the same dietary and oral care plan but did not chew the chewable composition. For some embodiments, the chewable composition preferably increases the ratio of the amount of *S. gordonii* to the amount of *S. mutans* in a biofilm in the oral cavity of an individual by about 5% or more within 8 hours of chewing the chewable composition for 45 seconds as compared to if the same individual proceeded with the same dietary and oral care plan but did not chew the chewable composition. Preferably, the ratio of the amount of *S. gordonii* to the amount of *S. mutans* is increased by about 10% or more, 15% or more, or 20% or more in a biofilm in the oral cavity of an individual within 8 hours of chewing the chewable composition for 45 seconds as compared to if the same individual proceeded with the same dietary and oral care plan but did not chew the chewable composition. Additionally, and without being limited to any specific theory, the chewable form of certain chewable compositions disclosed herein may further enhance the beneficial effects achieved by composition of chewable compositions, such as anti-caries effects.

In a first aspect, the present disclosure provides a chewable composition comprising an orally effective amount of arginine and an effective amount of a gelling agent. In certain embodiments, the gelling agent is an acidic polymer, e.g., a carboxylated polysaccharide. In certain embodiments, the gelling agent is selected from xanthan gum, gellan gum, pectin, carrageenan gum and combinations thereof, e.g., pectin. In certain embodiments, the arginine is present in an amount of about 0.001-5 wt. %, based on the total weight of the chewable oral care composition. The chewable composition may additionally comprise a calcium source, a polyhydric alcohol, and/or a nutrient source.

In another aspect, the present disclosure provides a method invention encompasses a method (Method 2) to improve oral health comprising applying an effective amount of the oral composition according to the present disclosure to the oral cavity of a subject in need thereof. In various embodiments, the applying step comprises chewing a chewable composition according to the present disclosure.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The features, and advantages of the invention will be apparent from the following more detailed description of certain embodiments of the invention and as illustrated in the accompanying drawings in which.

Figure 1:
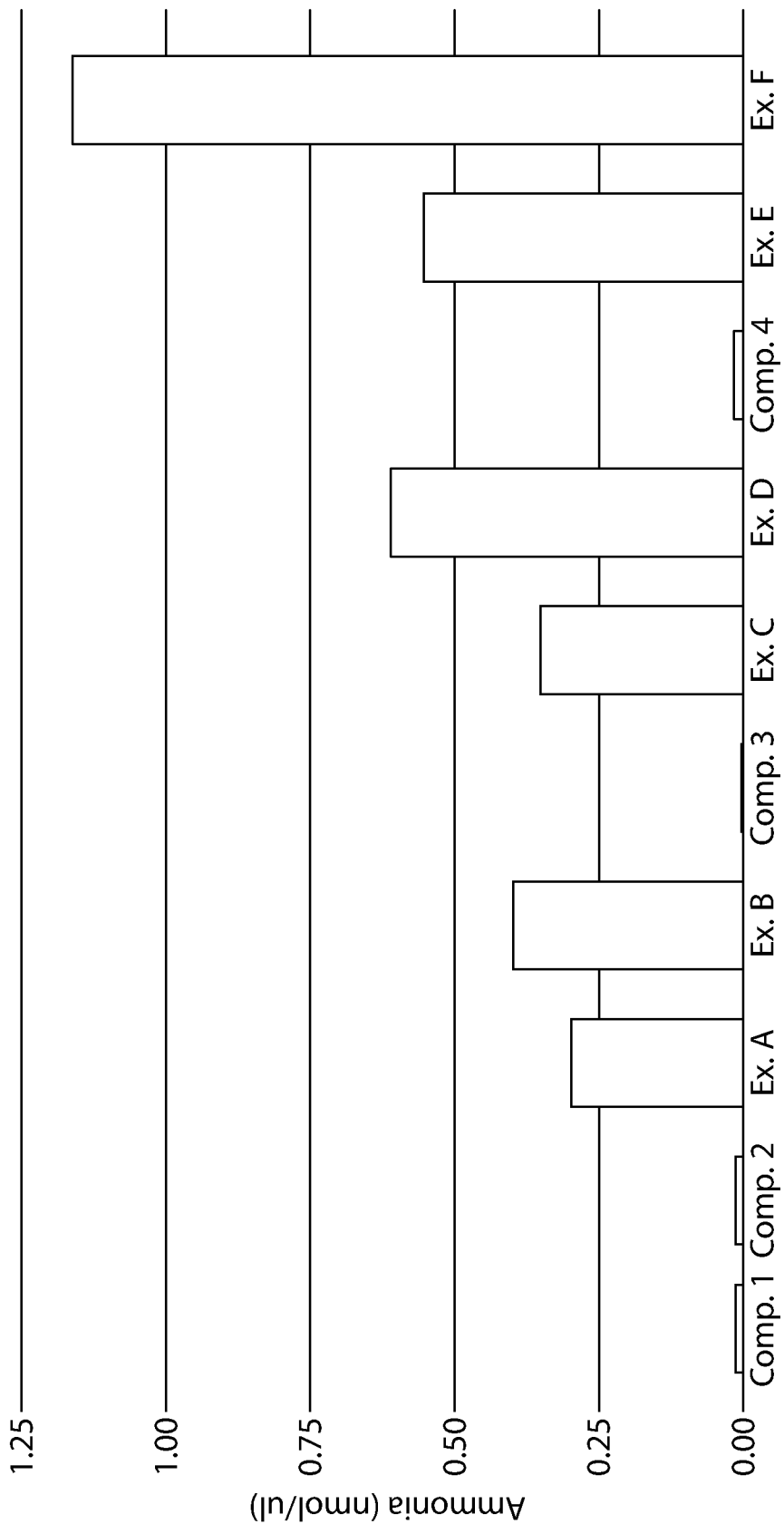
FIG. 1 is a bar graph showing the amount of ammonia production from exemplary chewable compositions and comparative chewable compositions in accordance with aspects of the invention.

It should be understood that the various aspects are not limited to the compositions, arrangements, and instrumentality shown in the figures.

DETAILED DESCRIPTION

The following description of the preferred embodiment(s) is merely exemplary in nature and is in no way intended to limit the disclosure, its application, or uses.

As used herein and in the appended claims, the singular forms "a", "an", and "the" include plural references unless the context dictates otherwise. The singular form of any class of the ingredients refers not only to one chemical species within that class, but also to a mixture of those chemical species. The terms "a" (or "an"), "one or more" and "at least one" may be used interchangeably herein. The terms "comprising", "including", and "having" may be used interchangeably. The term "include" should be interpreted as "include, but are not limited to". The term "including" should be interpreted as "including, but are not limited to".

As used throughout, ranges are used as shorthand for describing each and every value that is within the range. Any value within the range can be selected as the terminus of the range. Thus, a range from 1-5, includes specifically 1, 2, 3, 4 and 5, as well as subranges such as 2-5, 3-5, 2-3, 2-4, 1-4, etc.

The term "about" when referring to a number means any number within a range of 10% of the number. For example, the phrase "about 2 wt. %" refers to a number between and including 1.8 wt. % and 2.2 wt. %.

In addition, all references cited herein are hereby incorporated by referenced in their entireties. In the event of a conflict in a definition in the present disclosure and that of a cited reference, the present disclosure controls.

The abbreviations and symbols as used herein, unless indicated otherwise, take their ordinary meaning. The abbreviation "wt. %" means percent by weight with respect to the chewable composition. The symbol "°" refers to a degree, such as a temperature degree or a degree of an angle. The symbols "h", "min", "mL", "nm", "μm", "μL", "nmol" means hour, minute, milliliter, nanometer, micrometer, microliter, and nanomole, respectively. The abbreviation "UV-VIS" as referring to a spectrometer or spectroscopy, means Ultraviolet-Visible. The abbreviation "rpm" means revolutions per minute.

Any member in a list of species that are used to exemplify or define a genus, may be mutually different from, or overlapping with, or a subset of, or equivalent to, or nearly the same as, or identical to, any other member of the list of species. Further, unless explicitly stated, such as when reciting a Markush group, the list of species that define or exemplify the genus is open, and it is given that other species may exist that define or exemplify the genus just as well as, or better than, any other species listed.

The phrases, "a mixture thereof," "a combination thereof," or a combination of two or more thereof" do not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F." Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

All components and elements positively set forth in this disclosure can be negatively excluded from the claims. In other words, the chewable compositions of the instant disclosure can be free or essentially free of all components and elements positively recited throughout the instant disclosure. In some instances, the chewable compositions of the present disclosure may be substantially free of non-incidental amounts of the ingredient(s) or compound(s) described herein. A non-incidental amount of an ingredient or compound is the amount of that ingredient or compound that is added into the chewable composition by itself. For example, a chewable composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the chewable composition includes both components (or the composition includes more than two components that overlap), an overlapping compound does not represent more than one component. For example, xylitol may be characterized as both a sweetener and a polyhydric alcohol. If a particular chewable composition includes both a sweetener and a polyhydric alcohol, xylitol will serve only as either a sweetener or a polyhydric alcohol—not both.

For readability purposes, the chemical functional groups are in their adjective form; for each of the adjectives, the word "group" is assumed. For example, the adjective "alkyl" without a noun thereafter, should be read as "an alkyl group".

Unless otherwise specified, all percentages and amounts expressed herein and elsewhere in the specification should be understood to refer to percentages by weight relative to the total composition. The amounts given are based on the active weight of the material.

The present disclosure provides, in an aspect, chewable composition [Composition 1] comprising:
 a. an effective amount of an amino acid (e.g., a basic amino acid) (e.g., arginine); and
 b. an effective amount of a gelling agent (e.g., pectin).

For example, the disclosure includes:

1.1. Composition 1, wherein the basic amino acid is arginine, wherein the arginine is present in an amount of about 0.001-5 wt. %, based on the total weight of the composition.
1.2. Composition 1 or 1.1, wherein the arginine is present in an amount of about 0.01-2 wt. %, based on the total weight of the composition.
1.3. Any of the preceding compositions, wherein the arginine is present in an amount of about 0.1-0.5 wt. %, based on the total weight of the composition.
1.4. Any of the preceding compositions, wherein the arginine is present in an amount of about 0.35-0.45 wt. %, based on the total weight of the composition.
1.5. Any of the preceding compositions, wherein the arginine is present in an amount of about 0.37 wt. %, 0.38 wt. %, 0.39 wt. % or 0.4 wt. % (e.g., about 0.375 wt. %), based on the total weight of the composition.
1.6. Any of the preceding compositions, wherein the arginine has the L-configuration.
1.7. Any of the preceding compositions, wherein the arginine is in free base form.
1.8. Any of the preceding compositions, wherein the arginine is in the form of a salt.
1.9. Any of the preceding compositions, wherein the basic amino acid is arginine bicarbonate, arginine phosphate, arginine sulfate, arginine hydrochloride or combinations thereof, optionally wherein the basic amino acid is arginine bicarbonate.
1.10. Composition 1, wherein the basic amino acid selected from arginine, lysine, citrulline, ornithine, creatine, histidine, diaminobutyric acid, diaminopropionic acid, salts thereof, and combinations thereof.
1.11. Any of the preceding compositions, wherein the basic amino acid is selected from arginine, lysine, citrulline, and ornithine, and combinations thereof.
1.12. Any of the preceding compositions, wherein the basic amino acid has the L-configuration.
1.13. Any of the preceding compositions, wherein the gelling agent is an acidic polymer.
1.14. Any of the preceding compositions, wherein the gelling agent is a carboxylated polysaccharide.
1.15. Any of the preceding compositions, wherein the gelling agent is selected from xanthan gum, gellan gum, pectin, carrageenan gum and combinations thereof.
1.16. Any of the preceding compositions, wherein the gelling agent comprises or consists of pectin.
1.17. Any of the preceding compositions, wherein the gelling agent is present in an amount from 0.1-99 wt. %, based on the total weight of the composition.
1.18. Any of the preceding compositions, further comprising a polyhydric alcohol selected from glycerin, propylene glycol, polyethylene glycol, sorbitol, xylitol, erythritol, isomalt, lactitol, maltitol, mannitol, and combinations thereof.
1.19. Any of the preceding compositions, further comprising a polyhydric alcohol selected from glycerin, erythritol, sorbitol, xylitol, propylene glycol and combinations thereof.
1.20. Either of the two preceding compositions, wherein the polyhydric alcohol is present in an amount of about 1-50 wt. %, based on the total weight of the composition.
1.21. The preceding composition, wherein the polyhydric alcohol is xylitol.
1.22. The preceding compositions, wherein the xylitol is present in an amount of about 1-50 wt. %, based on the total weight of the composition.
1.23. Any of the preceding compositions, further comprising a calcium source.
1.24. The preceding composition, wherein the calcium source is selected from wherein the calcium source is selected from calcium carbonate, calcium bicarbonate, calcium phosphate (e.g., tricalcium phosphate or dicalcium phosphate, e.g., dicalcium phosphate dihydrate ($CaHPO_4 \cdot 2H_2O$)), calcium pyrophosphate, calcium sulfate and combinations thereof.
1.25. Any of the two preceding compositions, wherein the calcium source is selected from calcium carbonate, calcium bicarbonate, dicalcium phosphate (e.g., dicalcium phosphate dihydrate ($CaHPO_4 \cdot 2H_2O$)), calcium pyrophosphate, and combinations thereof.
1.26. Any of the three preceding compositions, wherein the calcium source comprises dicalcium phosphate.
1.27. The preceding composition, wherein the calcium source consists of dicalcium phosphate (e.g., dicalcium phosphate dihydrate ($CaHPO_4 \cdot 2H_2O$)).
1.28. Any of the preceding compositions, wherein the calcium source is present in an amount of about 0.1-50 wt. %, based on the total weight of the composition.
1.29. Any of the preceding compositions, further comprising a nutritional additive.
1.30. Any of the preceding compositions, further comprising a nutritional additive which is a vitamin or a mineral.
1.31. Any of the preceding compositions, wherein the nutritional additive is selected from vitamin A, vitamin C, vitamin D (e.g., vitamin $D_3$), vitamin E, vitamin K, vitamin $B_6$, vitamin $B_{12}$, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof.
1.32. Any of the preceding compositions, wherein the nutritional additive comprises or consists of vitamin $D_3$ and vitamin $B_{12}$.
1.33. Any of the preceding compositions, wherein the nutritional additive comprises or consists of vitamin $D_3$.

1.34. Any of the preceding compositions, wherein the nutritional additive comprises or consists of vitamin $B_{12}$.

1.35. Any of the preceding compositions, wherein the nutritional additive is present in an amount of about 1-50 wt. %, based on the total weight of the composition.

1.36. Any of the preceding compositions, wherein the composition is in the form of a gummy.

1.37. Any of the preceding compositions, wherein the composition is in the form of a unit dose sized to be administered orally and chewed by a person.

1.38. Any of the preceding compositions, wherein the composition is in the form of a unit dose which is ovoid, spherical, cylindrical, hemispherical, hexagonal, rectangular, cuboid, or otherwise polygonal or irregularly shaped.

1.39. Any of the preceding compositions, wherein the composition is in the form of a unit dose which is formed into an animal shape.

1.40. Any of the preceding compositions, comprising:
   a. arginine in an amount of about 0.01-2 wt. %, based on the total weight of the composition;
   b. a gelling agent comprising pectin;
   c. a polyhydric alcohol; and
   d. a calcium source.

1.41. Any of the preceding compositions, comprising:
   a. arginine in an amount of about 0.01-2 wt. %, based on the total weight of the composition;
   b. a gelling agent comprising pectin;
   c. a polyhydric alcohol comprising xylitol and/or erythritol;
   d. a calcium source comprising a calcium phosphate (e.g., dicalcium phosphate dihydrate ($CaHPO_4 \cdot 2H_2O$)); and
   e. optionally a nutritional source (e.g., vitamin $D_3$ and/or vitamin $B_{12}$).

1.42. Any of the preceding compositions, comprising:
   a. arginine in an amount of about 0.1-0.5 wt. %, based on the total weight of the composition;
   b. a gelling agent comprising pectin;
   c. a polyhydric alcohol comprising xylitol;
   d. a calcium source comprising dicalcium phosphate dihydrate ($CaHPO_4 \cdot 2H_2O$); and
   e. optionally a nutritional source (e.g., vitamin $D_3$ and/or vitamin $B_{12}$).

1.43. Any of the preceding compositions, comprising:
   a. arginine in an amount of about 0.35-0.45 wt. %, based on the total weight of the composition;
   b. a gelling agent comprising pectin;
   c. a polyhydric alcohol comprising xylitol;
   d. a calcium source comprising dicalcium phosphate dihydrate ($CaHPO_4 \cdot 2H_2O$); and
   e. optionally a nutritional source (e.g., vitamin $D_3$ and/or vitamin $B_{12}$).

1.44. Any of the preceding compositions where the amount of the amino acid is effective to be incorporated within a final gel.

1.45. Any of the preceding compositions where the amount of the gelling agent is effective to form a gel and incorporate the amino acid.

1.46. Any of the preceding compositions further comprising a fluoride source selected from: stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof.

1.47. Any of the preceding compositions wherein the fluoride source is a fluorophosphate.

1.48. Any of the preceding compositions wherein the fluoride source is sodium monofluorophosphate.

1.49. Any of the preceding compositions wherein the fluoride source is sodium fluoride.

1.50. Any of the preceding compositions wherein the fluoride source is stannous fluoride.

1.51. Any of the preceding compositions wherein the fluoride source is a fluoride salt present in an amount of 0.1 wt. % to 2 wt. % (0.1 wt. %-0.6 wt. %) of the total composition weight (e.g., sodium fluoride (e.g., about 0.3 wt. %) or sodium monofluorophosphate).

In another embodiment, the invention encompasses a method [Method 1] to improve oral health comprising applying an effective amount of the oral composition of any of the embodiments under Compositions 1, et seq., to the oral cavity of a subject in need thereof, e.g., a method to
   i. reduce or inhibit formation of dental caries,
   ii. reduce, repair or inhibit early enamel lesions, e.g., as detected by quantitative light-induced fluorescence (QLF) or electrical caries measurement (ECM),
   iii. reduce or inhibit demineralization and promote remineralization of the teeth,
   iv. reduce hypersensitivity of the teeth,
   v. reduce or inhibit gingivitis,
   vi. promote healing of sores or cuts in the mouth,
   vii. reduce levels of acid producing bacteria,
   viii. to increase relative levels of arginolytic bacteria,
   ix. inhibit microbial biofilm formation in the oral cavity,
   x. raise and/or maintain plaque pH at levels of at least about pH 5.5 following sugar challenge,
   xi. reduce plaque accumulation,
   xii. enhance systemic health, including cardiovascular health, e.g., by reducing potential for systemic infection via the oral tissues,
   xiii. immunize the teeth against cariogenic bacteria,
   xiv. clean the teeth and oral cavity;
   xv. improve the appearance of teeth; and/or
   xvi preempt and/or mitigate plaque acid attack.

The invention further comprises the use of arginine in the manufacture of Composition 1, et seq., for use in any of the indications set forth in Method 1.

The invention further provides Composition 1, et seq., for reducing the adhesion of bacteria to tooth surfaces in an oral cavity of a subject.

The invention further provides the use of Composition 1, et seq., for reducing the adhesion of bacteria to tooth surfaces in an oral cavity of a subject.

The invention further provides the use of Composition 1, et seq., for the manufacture of a medicament, for use in reducing the adhesion of bacteria to tooth surfaces in an oral cavity of a subject.

The invention further provides a method of reducing the adhesion of bacteria to tooth surfaces in an oral cavity of a subject, the method comprising treating the oral cavity with Composition 1, et seq.

The invention further provides a kit [Kit 1] comprising:
   a) one or more unit doses of a chewable composition (e.g., Composition 1 et seq.), in the form of a gummy; and
   b) a container sized to hold the one or more unit doses of the chewable composition.

For example, the disclosure includes:

1.1 Kit 1, wherein the kit contains at least 5, at least 10, at least 20, at least 30, at least 40, at least 50, at least 60, at least 70, at least 80, at least 90, or at least 100 unit doses of the chewable composition.

1.2 Kit 1 or 1.1, wherein the unit doses are sized to be administered orally and chewed by a person.

1.3 Any of the preceding kits, wherein the unit doses are ovoid, spherical, cylindrical, hemispherical, hexagonal, rectangular, cuboid, or otherwise polygonal or irregularly shaped.

1.4 Any of the preceding kits, wherein the unit doses are formed into animal shapes.

The term "chewable composition" as used herein means a composition that is suitable for chewing in the oral cavity of an individual and/or animal. For example, the chewable composition may be in the form of a gummy, chewable soft candy confection, chewy candy and the like. The chewable compositions of the present disclosure encompass molded gummy or gelatinous forms. In some instances, the chewable compositions are in a form that is hard and/or brittle. Although the chewable composition is typically edible and/or ingestible, in some instances the chewable composition is inedible and/or indigestible. For instance, the chewable composition may be inedible and/or indigestible and should be discharged after chewing, e.g., via spitting. Additionally or alternatively, the chewable compositions are typically oral compositions. For example, the chewable compositions are generally adapted to be chewed in the oral cavity of an individual and/or animal.

As used herein, the term "edible composition" refers to a composition that is suitable for being swallowed by an individual and/or animal. The edible compositions disclosed herein are typically chewable compositions, although in some cases the edible composition is not a chewable composition.

All ingredients for use in the compositions described herein should be orally acceptable. As used herein, "orally acceptable" may refer to any ingredient that is present in a composition as described in an amount and form which does not render the composition unsafe for use in the oral cavity.

As used herein, an "oral care composition" refers to a composition for which the intended use includes oral care, oral hygiene, and/or oral appearance, or for which the intended method of use comprises administration to the oral cavity, and refers to compositions that are palatable and safe for topical administration to the oral cavity, and for providing a benefit to the teeth and/or oral cavity. The term "oral care composition" thus specifically excludes compositions which are highly toxic, unpalatable, or otherwise unsuitable for administration to the oral cavity. In some embodiments, an oral care composition is not intentionally swallowed, but is rather retained in the oral cavity for a time sufficient to affect the intended utility. The oral care compositions as disclosed herein may be used in nonhuman mammals such as companion animals (e.g., dogs and cats), as well as by humans. In some embodiments, the oral care compositions as disclosed herein are used by humans.

Suitable components, such as those listed below, may be included or excluded from the formulations for the chewable compositions depending on the specific combination of other ingredients, the form of the chewable compositions, and/or the use of the compositions (e.g., as an oral care product, as a nutritional supplement, or the like).

The chewable compositions of the present disclosure may be configured to be chewed to deliver the active agent (e.g., a basic amino acid, such as arginine) to the surface of the teeth in order to impart an anti-caries effect. Additionally or alternatively, the chewable compositions may be configured to be chewed to facilitate delivery and/or absorption of the active ingredient in the oral cavity and/or in the digestive system. In some embodiments, the disclosed chewable compositions are configured to release arginine through mastication, through dissolving upon contact with saliva or a combination thereof. In some embodiments, the disclosed chewable compositions are configured to melt or be chewed in an oral cavity therefore provide a chewing time not less than 10 seconds, 20 seconds, 30 seconds, 40 seconds, 50 seconds, or 1, 2, 3, 4, 5, 6, 7, 8, 9, or 10 minutes. In at least one embodiment, the chewable compositions are configured to be chewed for about 30 to about 90 seconds, e.g., about 30 to about 70 seconds, about 30 to about 50 seconds, about 40 to about 50 seconds, or about 45 seconds.

The chewable composition of the disclosure may be formulated to be chewed by a person such that it is broken up into smaller parts or melts within the oral cavity causing the release of the basic amino acid to the surface of the teeth. Once broken up or partially melted, the smaller pieces may be easily swallowed. In certain embodiments, the compositions of the present disclosure have a sufficiently high viscosity such that it does not flow or otherwise conform to its container at room temperature. For instance, the composition may be formulated such that it does not flow at low shear stress and generally exhibits plastic flow behavior.

The chewable composition may be formulated to have a hardness, associated with a peak force of about 50 to about 150 grams for a 10% strain in the form of the chewable composition. For instance, the chewable composition may have a peak force at a 10% strain of about 50 to about 150 grams, about 50 to about 130 grams, about 50 to about 120 grams, about 50 to about 110 grams, about 50 to about 100 grams, about 50 to about 90 grams; from about 60 to about 150 grams, about 60 to about 130 grams, about 60 to about 120 grams, about 60 to about 110 grams, about 60 to about 100 grams, about 60 to about 90 grams; from about 70 to about 150 grams, about 70 to about 130 grams, about 70 to about 120 grams, about 70 to about 110 grams, about 70 to about 100 grams, about 70 to about 90 grams; from about 80 to about 150 grams, about 80 to about 130 grams, about 80 to about 120 grams, about 80 to about 110 grams, about 80 to about 100 grams, about 80 to about 90 grams, or any range or subrange thereof.

The chewable compositions may, additionally or alternatively, have a hardness, associated with a peak force of about 400 to about 1100 grams for a 50% strain in the form of the chewable composition. In some instances, the chewable composition has a peak force at a 50% strain of about 400 to about 1100 grams, about 400 to about 1000 grams, about 400 to about 950 grams, about 400 to about 900 grams, about 400 to about 850 grams, about 400 to about 800 grams, about 400 to about 750 grams, about 400 to about 700 grams, about 400 to about 650 grams, about 400 to about 600 grams, about 400 to about 550 grams; from about 500 to about 1100 grams, about 500 to about 1000 grams, about 500 to about 950 grams, about 500 to about 900 grams, about 500 to about 850 grams, about 500 to about 800 grams, about 500 to about 750 grams, about 500 to about 700 grams, about 500 to about 650 grams, about 500 to about 600 grams; from about 550 to about 1100 grams, about 550 to about 1000 grams, about 550 to about 950 grams, about 550 to about 900 grams, about 550 to about 850 grams, about 550 to about 800 grams, about 550 to about 750 grams, about 550 to about 700 grams, about 550 to about 650 grams; from about 600 to about 1100 grams, about 600 to about 1000 grams, about 600 to about 950 grams, about 600 to about 900 grams, about 600 to about 850 grams, about 600 to about 800 grams, about 600 to about 750 grams, about 600 to about 700 grams, or any range or subrange thereof.

The chewable compositions may be formulated to have a resilience value, e.g., from about 5% to about 65%. The resilience value may be determined based on texture profile analysis (TPA) test using, e.g., a texturometer TA.XT.Plus from Stable Micro Systems (Godalming, United Kingdom), with a flat cylindrical probe P/75 by measuring force on compression using a 50 kg load cell, a trigger force of 0.05 N, a compression distance of 5 mm, a pretest speed of 0.5 mm/s, a test speed of 0.5 mm/s, and a posttest speed of 0.5 mm/s. Additionally or alternatively, the resilience value may be determined based on a perforation test with a 2 mm diameter probe P2 by measuring force on compression using a 50 kg load cell, a trigger force of 0.05 N, a perforation distance of 3 mm, a pretest speed of 2.0 mm/s, a test speed of 1.0 mm/s, and a posttest speed of 1.0 mm/s. In some embodiments, the chewable compositions have a resilience value of from about 5 to about 65%, about 5 to about 55%, about 5 to about 50%, about 5 to about 45%, about 5 to about 35%, about 5 to about 25%, about 5 to about 15%; from about 10 to about 65%, about 10 to about 55%, about 10 to about 50%, about 10 to about 45%, about 10 to about 35%, about 10 to about 25%; from about 20 to about 65%, about 20 to about 55%, about 20 to about 50%, about 20 to about 45%, about 20 to about 35%; from about 30 to about 65%, about 30 to about 55%, about 30 to about 50%, about 30 to about 45%; from about 40 to about 65%, about 40 to about 55%, about 40 to about 50%; from about 50 to about 65%, about 50 to about 55%, or any range or subrange thereof, based on a texture profile analysis or perforation test, wherein the texture profile analysis uses a flat cylindrical probe P/75 by measuring force on compression using a 50 kg load cell, a trigger force of 0.05 N, a compression distance of 5 mm, a pretest speed of 0.5 mm/s, a test speed of 0.5 mm/s, and a posttest speed of 0.5 mm/s, and wherein the perforation test uses a 2 mm diameter probe P2 by measuring force on compression using a 50 kg load cell, a trigger force of 0.05 N, a perforation distance of 3 mm, a pretest speed of 2.0 mm/s, a test speed of 1.0 mm/s, and a posttest speed of 1.0 mm/s.

It is envisioned that the composition may have any size and shape such that it can be administered orally and/or chewed by a person. The chewable compositions may be formulated such that a person should be able to readily break apart the composition dosage by chewing the composition dosage without the need for an external source of liquid. Although the chewable compositions are typically configured to be chewed and swallowed, in some embodiments the chewable compositions are configured to be chewed and then expelled from the oral cavity, e.g., via spitting. Typically, the composition dosage has a length of about 1 cm to about 5 cm, width of about 1 cm to about 5 cm and a height of about 1 cm to about 5 cm. Suitable shapes include geometric shapes, for example, ovals, spheres, cylinders, hemisphere, hexagon, rectangular boxes, cubes, or otherwise polygonal shapes; substantially geometric shapes, or irregular shapes. The composition dosage may be formed into unique shapes and figures including, for example, animals for administration to children (e.g., under the age of 13) and/or adults.

The composition of the disclosure may be administered once per day or multiple times per day as necessary to impart an anti-caries effect. For example, a person may consume one or more unit doses of the composition after eating, e.g., after each meal. In some embodiments, a person may consume one or more unit doses of the composition periodically, e.g., hourly.

Water may be present in the chewable compositions of the disclosure. Water employed in the preparation of chewable compositions may, in some instances, be deionized and free of organic impurities. Water may make up the balance of the chewable compositions and includes about 1 to about 80 wt. %, about 20 to about 60 wt. %, about 20 to about 40 wt. %, about 10 to about 30 wt. %, about 20 to about 30 wt. %, or about 25 to about 35 wt. %, by weight of the oral compositions. In certain embodiments, the chewable composition of the present disclosure includes water in an amount of less than about 15 wt. %, e.g., about 14 wt. % or less, about 13 wt. % or less, about 12 wt. % or less, about 11 wt. % or less, about 10 wt. % or less, about 9 wt. % or less, about 8 wt. % or less, about 7 wt. % or less, about 6 wt. % or less, or about 5 wt. % or less, based on the total weight of the chewable composition. Certain embodiments of the chewable compositions may be substantially free of water. For instance, the chewable composition may have water present in an amount of about 4 wt. % or less, about 3 wt. % or less, about 2 wt. % or less, or about 1 wt. % or less, based on the total weight of chewable composition. This amount of water includes the free water which is added plus that amount which is introduced with other materials or any components according to the present disclosure.

In one aspect, the chewable compositions of the disclosure comprise a basic amino acid in free and/or salt form. The chewable composition may include one or more amino acid(s) in an amount that may vary, but typically is present in an amount from about 0.01 to about 20 wt. %, based on the total weight of the chewable composition. For example, the total amount of amino acid(s) in the chewable composition may be from about 0.01 to about 20 wt. %, about 0.01 to about 16 wt. %, about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %, about 0.01 to about 0.5 wt. %; from about 0.05 to about 20 wt. %, about 0.05 to about 16 wt. %, about 0.05 to about 12 wt. %, about 0.05 to about 10 wt. %, about 0.05 to about 8 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.05 to about 0.5 wt. %; from about 0.1 to about 20 wt. %, about 0.1 to about 16 wt. %, about 0.1 to about 12 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %; from about 0.3 to about 20 wt. %, about 0.3 to about 16 wt. %, about 0.3 to about 12 wt. %, about 0.3 to about 10 wt. %, about 0.3 to about 8 wt. %, about 0.3 to about 6 wt. %, about 0.3 to about 5 wt. %, about 0.3 to about 4 wt. %, about 0.3 to about 3 wt. %, about 0.3 to about 2 wt. %, about 0.3 to about 1 wt. %, about 0.3 to about 0.5 wt. %; from about 0.5 to about 20 wt. %, about 0.5 to about 16 wt. %, about 0.5 to about 12 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 20 wt. %, about 1 to about 16 wt. %, about 1 to about 12 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; from about 3 to about 20 wt. %, about 3 to about 16 wt. %, about 3 to about 12 wt. %, about 3 to about 10 wt. %, about 3 to about 8 wt. %, about 3 to about 6 wt. %, about 3 to about 5 wt. %; from about 5 to about 20 wt. %, about 5 to about 16 wt. %, about 5 to about 12 wt. %, about 5 to about 10 wt. %, about 5 to about 8 wt. %; from about 9 to about 20 wt. %, about 9 to about 16 wt. %, about 9 to about 12 wt. %; from about 14 to about 20 wt. %, about 14 to about 16 wt. %; from about 16 to about 20 wt. %, about 16 to about 18 wt. %, or any range or subrange thereof, based on the total weight of the chewable composition. In some embodiments, the basic amino acid is present in an amount of from 0.001% to 5%, e.g., from 0.01% to 2%, from 0.1% to 0.5%, from 0.35% to 0.45%, e.g., about 0.37 wt. %, about 0.38 wt. %, about 0.39 wt. % or about 0.4 wt. % (e.g., about 0.375 wt. %), based on the total weight of the composition by weight of the composition, being calculated as free base form.

The basic amino acids which can be used in the compositions include not only naturally occurring basic amino acids, such as arginine, lysine, and histidine, but also any basic amino acids having a carboxyl group and an amino group in the molecule, which are water-soluble and provide an aqueous solution with a pH of about 7 or greater. Exemplary, non-limiting basic amino acids include, but are not limited to, arginine, lysine, citrulline, ornithine, creatine, histidine, diaminobutyric acid, diaminopropionic acid, salts thereof or combinations thereof. Additional examples of amino acids that may be included in the chewable composition include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, a salt thereof, or combinations of two or more thereof.

The chewable compositions may include two or more amino acids, e.g., three, four, five, six, seven, or eight or more amino acids, including any range or subrange therefrom. For instance, the chewable composition may include arginine and/or a salt thereof and one or more amino acids and/or salts thereof selected from alanine, asparagine, aspartic acid, cysteine, glutamine, glutamic acid, glycine, histidine, isoleucine, leucine, lysine, methionine, phenylalanine, proline, serine, threonine, tryptophan, tyrosine, valine, a salt thereof, or combinations of two or more thereof. In some embodiments, the amino acids comprise arginine and/or a salt thereof and at least one of lysine, citrulline, ornithine, a salt thereof, or a combination of two or more thereof. In further embodiments, the chewable composition includes one or more basic amino acid(s) and in addition to the basic amino acid(s) included in the formulation, the chewable composition of the disclosure (e.g., any of Compositions 1.0 et seq.) can further include a neutral amino acid(s), which can include, but are not limited to, one or more neutral amino acid(s) selected from the group consisting of alanine, aminobutyrate, asparagine, cysteine, cystine, glutamine, glycine, hydroxyproline, isoleucine, leucine, methionine, phenylalanine, proline, serine, taurine, threonine, tryptophan, tyrosine, valine, and combinations thereof. In a particular embodiment, the basic amino acids are selected from arginine, lysine, citrulline, and ornithine.

Preferably, the chewable compositions comprise arginine and/or a salt thereof. In some embodiments, the amino acid is arginine, for example, L-arginine, or a salt thereof. Arginine may be provided as free arginine or a salt thereof. For example, arginine may be provided as arginine phosphate, arginine hydrochloride, arginine sulfate, arginine bicarbonate, or the like, and mixtures or combinations thereof.

The chewable compositions may include arginine in any of the amounts described above with respect to the amino acid(s). For embodiments containing two or more amino acids, the two or more amino acids may be present in the chewable compositions in the amounts described above with respect to the amino acids on an individual or combination basis.

The amino acids of the chewable composition may generally be present in the L-form or L-configuration. The chewable composition may include one or more basic amino acid(s). As referred herein, a basic amino acid contains basic side chains at the neutral pH. An acid amino acid contains acidic side chains at the neutral pH. The basic amino acids may be provided as a salt of a di- or tri-peptide including the amino acid. In some embodiments, at least a portion of the amino acid (e.g. basic amino acid) present in the chewable composition is in the salt form.

The amino acid (e.g., basic amino acid) may be provided as a solution or a solid. For example, the amino acid (e.g., basic amino acid) may be provided as an aqueous solution. In some embodiments, the amino acid includes or is provided by an arginine bicarbonate solution. For example, the solution containing the amino acid may contain arginine in an amount of about 40 wt. %, based on the total weight of solution, such as arginine bicarbonate solution or alternatively called as arginine carbamate solution.

The chewable compositions as disclosed herein typically comprise a gelling agent. Any suitable gelling agent may be used to provide the dosage form with the desired characteristics including, for example, semi-solid structure, shape and texture. Polysaccharides, and gelling agents more generally, used in the manufacture of chewable compositions have the ability to form a gel under certain conditions. Gelation refers to the formation of a gel from individual polysaccharides. During gelation, polysaccharides form links between one another, which can lead to progressively larger polysaccharide networks. As the linking continues, larger branched polymers may be obtained and at a certain extent of the reaction links between the polymer result in the formation of a single macroscopic molecule.

The amount of gelling agent in the chewable composition may vary, but typically ranges from about 0.01 to about 20 wt. %, based on the total weight of the chewable composition. For example, the total amount of gelling agent(s) in the chewable composition may be from about 0.01 to about 20 wt. %, about 0.01 to about 16 wt. %, about 0.01 to about 12 wt. %, about 0.01 to about 10 wt. %, about 0.01 to about 8 wt. %, about 0.01 to about 6 wt. %, about 0.01 to about 5 wt. %, about 0.01 to about 4 wt. %, about 0.01 to about 3 wt. %, about 0.01 to about 2 wt. %, about 0.01 to about 1 wt. %, about 0.01 to about 0.5 wt. %; from about 0.05 to about 20 wt. %, about 0.05 to about 16 wt. %, about 0.05 to about 12 wt. %, about 0.05 to about 10 wt. %, about 0.05 to about 8 wt. %, about 0.05 to about 6 wt. %, about 0.05 to about 5 wt. %, about 0.05 to about 4 wt. %, about 0.05 to about 3 wt. %, about 0.05 to about 2 wt. %, about 0.05 to about 1 wt. %, about 0.05 to about 0.5 wt. %; from about 0.1 to about 20 wt. %, about 0.1 to about 16 wt. %, about 0.1 to about 12 wt. %, about 0.1 to about 10 wt. %, about 0.1 to about 8 wt. %, about 0.1 to about 6 wt. %, about 0.1 to about 5 wt. %, about 0.1 to about 4 wt. %, about 0.1 to about 3 wt. %, about 0.1 to about 2 wt. %, about 0.1 to about 1 wt. %, about 0.1 to about 0.5 wt. %; from about 0.3 to about 20 wt. %, about 0.3 to about 16 wt. %, about 0.3 to about 12 wt. %, about 0.3 to about 10 wt. %, about 0.3 to about 8 wt. %, about 0.3 to about 6 wt. %, about 0.3 to about 5 wt. %, about 0.3 to about 4 wt. %, about 0.3 to about 3 wt. %, about 0.3 to about 2 wt.

%, about 0.3 to about 1 wt. %, about 0.3 to about 0.5 wt. %; from about 0.5 to about 20 wt. %, about 0.5 to about 16 wt. %, about 0.5 to about 12 wt. %, about 0.5 to about 10 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 20 wt. %, about 1 to about 16 wt. %, about 1 to about 12 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; from about 3 to about 20 wt. %, about 3 to about 16 wt. %, about 3 to about 12 wt. %, about 3 to about 10 wt. %, about 3 to about 8 wt. %, about 3 to about 6 wt. %, about 3 to about 5 wt. %; from about 5 to about 20 wt. %, about 5 to about 16 wt. %, about 5 to about 12 wt. %, about 5 to about 10 wt. %, about 5 to about 8 wt. %; from about 9 to about 20 wt. %, about 9 to about 16 wt. %, about 9 to about 12 wt. %; from about 14 to about 20 wt. %, about 14 to about 16 wt. %; from about 16 to about 20 wt. %, about 16 to about 18 wt. %, or any range or subrange thereof, based on the total weight of the chewable composition.

The gelling agent is typically a USP (U.S. Pharmacopeia) grade gelling agent. The gelling agent may be selected from polysaccharides, peptides, hydrocolloids, and combinations thereof. Examples of gelling agents include alginate, seaweed extract (e.g., pectin), carrageenan, gellan, gelatin, agar, modified starch, methylcellulose, hydroxypropylmethyl cellulose, xanthan gum, gum tragacanth, and any combinations thereof. In some instances, the chewable composition includes at least one gelling agent selected from pectin, gelatin, seaweed extract, agar, carrageenan, gum Arabic, and any combinations thereof. Preferably, the gelling agent comprises pectin.

The chewable composition may include two or more gelling agents. For example, the chewable composition may include two or more, such as three, four, five, six, seven, eight, nine, or ten or more gelling agents. The chewable composition may include two to ten, two to eight, two to six, or two to four gelling agents, including any range or subrange thereof. In various embodiments, the gelling agent is an acidic polymer, e.g., a carboxylated polysaccharide. For example, the gelling agent may be selected from xanthan gum, gellan gum, pectin, carrageenan gum and combinations thereof. In some embodiments, the chewable composition includes one or more gelling agent other than pectin. The amount of pectin and/or gelling agent(s) other than pectin may be present in the chewable composition in any of the amounts, individually or in combination, described above with reference to the gelling agent. In some instances, pectin may be present in the gummy composition dosage in an amount of from about 0.01% by weight to about 10% by weight. In some embodiments, pectin is present in an amount of from about 0.5% by weight to about 7% by weight, for example from about 0.5% to about 1%, from about 1% to about 1.5%, from about 1.5% to about 2%, from about 2% to about 2.5%, from about 2.5% to about 3%, from about 3% to about 3.5%, from about 3.5% to about 4%, from about 4% to about 4.5%, from about 4.5% to about 5%, from about 5% to about 5.5%, from about 5.5% to about 6%, from about 6% to about 6.5%, and from about 6.5% to about 7%. In one embodiment, pectin is present in an amount from about 1% by weight to about 5% by weight.

The chewable composition may be formulated to have a weight ratio of the total amount of the gelling agent selected from pectin, carrageenan, and a combination thereof to total amount of arginine and/or salt thereof ranging from about 25:1 to about 1:1. Preferably, the weight ratio of the total amount of the gelling agent selected from pectin, carrageenan, and a combination thereof to total amount of arginine and/or salt thereof is from about 23:1 to about 1:1, about 21:1 to about 1:1, about 20:1 to about 1:1, about 18:1 to about 1:1, about 16:1 to about 1:1, about 14:1 to about 1:1, about 12:1 to about 1:1, about 10:1 to about 1:1, about 8:1 to about 1:1, about 7:1 to about 1:1, about 6:1 to about 1:1, about 5:1 to about 1:1, about 4:1 to about 1:1, about 3:1 to about 1:1, about 2:1 to about 1:1; from about 23:1 to about 1.5:1, about 21:1 to about 1.5:1, about 20:1 to about 1.5:1, about 18:1 to about 1.5:1, about 16:1 to about 1.5:1, about 14:1 to about 1.5:1, about 12:1 to about 1.5:1, about 10:1 to about 1.5:1, about 8:1 to about 1.5:1, about 7:1 to about 1.5:1, about 6:1 to about 1.5:1, about 5:1 to about 1.5:1, about 4:1 to about 1.5:1, about 3:1 to about 1.5:1; from about 23:1 to about 2:1, about 21:1 to about 2:1, about 20:1 to about 2:1, about 18:1 to about 2:1, about 16:1 to about 2:1, about 14:1 to about 2:1, about 12:1 to about 2:1, about 10:1 to about 2:1, about 8:1 to about 2:1, about 7:1 to about 2:1, about 6:1 to about 2:1, about 5:1 to about 2:1, about 4:1 to about 2:1, about 3:1 to about 2:1, including ranges and subranges thereof. In some embodiments, the weight ratio of the total amount of the gelling agent selected from pectin, carrageenan, and a combination thereof to the total amount of arginine and/or salt thereof is from about 23:1 to about 1:1, about 21:1 to about 1:1, about 20:1 to about 1:1, about 20:1 to about 1.5:1, or about 20:1 to about 2:1.

Additionally and/or alternatively, the total amount of gelling agent to total amount of arginine and/or salt thereof may range from about 25:1 to about 1:1 about 23:1 to about 1:1, about 21:1 to about 1:1, about 20:1 to about 1:1, about 20:1 to about 1.5:1, or about 20:1 to about 2:1. For example, the weight ratio of the total amount of the gelling agent to the total amount of arginine and/or salt thereof may be from about 23:1 to about 1:1, about 21:1 to about 1:1, about 20:1 to about 1:1, about 18:1 to about 1:1, about 16:1 to about 1:1, about 14:1 to about 1:1, about 12:1 to about 1:1, about 10:1 to about 1:1, about 8:1 to about 1:1, about 7:1 to about 1:1, about 6:1 to about 1:1, about 5:1 to about 1:1, about 4:1 to about 1:1, about 3:1 to about 1:1, about 2:1 to about 1:1; from about 23:1 to about 1.5:1, about 21:1 to about 1.5:1, about 20:1 to about 1.5:1, about 18:1 to about 1.5:1, about 16:1 to about 1.5:1, about 14:1 to about 1.5:1, about 12:1 to about 1.5:1, about 10:1 to about 1.5:1, about 8:1 to about 1.5:1, about 7:1 to about 1.5:1, about 6:1 to about 1.5:1, about 5:1 to about 1.5:1, about 4:1 to about 1.5:1, about 3:1 to about 1.5:1; from about 23:1 to about 2:1, about 21:1 to about 2:1, about 20:1 to about 2:1, about 18:1 to about 2:1, about 16:1 to about 2:1, about 14:1 to about 2:1, about 12:1 to about 2:1, about 10:1 to about 2:1, about 8:1 to about 2:1, about 7:1 to about 2:1, about 6:1 to about 2:1, about 5:1 to about 2:1, about 4:1 to about 2:1, about 3:1 to about 2:1, including ranges and subranges thereof.

In some embodiments, the chewable composition of the disclosure comprises a calcium-source. In some embodiments, the calcium source is selected from calcium carbonate, calcium bicarbonate, calcium phosphate (e.g., dicalcium phosphate dihydrate), calcium sulfate, and combinations thereof. In some embodiments, the chewable composition comprises calcium phosphate. In some embodiments, the chewable composition comprises dicalcium phosphate dihydrate.

The amount of calcium in the chewable composition may vary, but generally ranges from about 0.5 to about 20 wt. %, based on the total weight of the chewable composition. For example, the total amount of calcium source in the chewable composition may be from about 0.5 to about 18 wt. %, about 0.5 to about 16 wt. %, about 0.5 to about 14 wt. %, about 0.5 to about 12 wt. %; from about 2 to about 20 wt. %, about 2 to about 18 wt. %, about 2 to about 16 wt. %, about 2 to about 14 wt. %, about 2 to about 12 wt. %; from about 4 to about 20 wt. %, about 4 to about 18 wt. %, about 4 to about 16 wt. %, about 4 to about 14 wt. %, about 4 to about 12 wt. %; from about 6 to about 20 wt. %, about 6 to about 18 wt. %, about 6 to about 16 wt. %, about 6 to about 14 wt. %, about 6 to about 12 wt. %; from about 8 to about 20 wt. %, about 8 to about 18 wt. %, about 8 to about 16 wt. %, about 8 to about 14 wt. %, about 8 to about 12 wt. %; from about 9 to about 20 wt. %, about 9 to about 18 wt. %, about 9 to about 16 wt. %, about 9 to about 14 wt. %, about 9 to about 12 wt. %, about 9 to about 11 wt. %; from about 0.5 to about 8 wt. %, about 0.5 to about 8 wt. %, about 0.5 to about 6 wt. %, about 0.5 to about 5 wt. %, about 0.5 to about 4 wt. %, about 0.5 to about 3 wt. %, about 0.5 to about 2 wt. %, about 0.5 to about 1 wt. %; from about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %; from about 3 to about 10 wt. %, about 3 to about 8 wt. %, about 3 to about 6 wt. %, about 3 to about 5 wt. %; from about 5 to about 10 wt. %, about 5 to about 8 wt. %; from about 9 to about 20 wt. %, about 7 to about 10 wt. %, about 7 to about 8.5 wt. %, or any range or subrange thereof, based on the total weight of the chewable composition.

In some embodiments, the chewable composition of the disclosure may include one or more polyhydric alcohol. Illustrative polyhydric alcohols may be or include, but are not limited to, glycerin, propylene glycol, polyethylene glycol, sorbitol, xylitol, erythritol, isomalt, lactitol, maltitol, mannitol, or the like, or any mixture or combination thereof. In a preferred embodiment, the polyhydric alcohol may be or include, but is not limited to, xylitol. In some embodiments, the polyhydric alcohol is selected from xylitol, erythritol and a combination thereof. In some embodiments, the polyhydric alcohol may be present in an amount of from about 1 to about 60 wt. %, for example from about 15 to about 40 wt. %, from about 15 to about 35 wt. %, from about 20 to about 40 wt. %, from about 30 to about 50 wt. %, from about 30 to about 40 wt. %, or from about 40 to about 45 wt. %, by weight of the chewable composition. In some embodiments, the chewable composition comprises xylitol and/or glycerin in an amount of from 15% to 40%, from 20% to 40%, from 30% to 40%, or about 35% by weight of the chewable composition. In further embodiments, the xylitol and/or glycerin may be present from about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 10 wt. %, about 1 to about 8 wt. %, about 1 to about 6 wt. %, about 1 to about 4 wt. %, about 1 to about 2 wt. %, including ranges and subranges thereof, based on the total weight of the chewable composition.

The chewable composition of the present disclosure may include a preservative. Suitable preservatives include, but are not limited to, sodium benzoate, potassium sorbate, methylisothiazolinone, paraben preservatives, for example methyl p-hydroxybenzoate, propyl p-hydroxybenzoate, and mixtures thereof.

In various embodiments, the present chewable compositions may comprise one or more nutritional additives. It is envisioned that the chewable compositions of the present disclosure may include virtually any vitamin or mineral. For example, vitamin A, vitamin C, vitamin D, vitamin E, vitamin K, vitamin B6, vitamin D3, vitamin Biz, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used. In further embodiments, the chewable composition comprises nutritional additive including, but not limited to, an herbal extract, an herb powder, a natural product, a vitamin, an amino acid, a lipid, a fatty acid, an enzyme, a co-enzyme, a hormone, and/or an antioxidant. Non-limiting examples of nutritional ingredients include, but are not limited to, herbal additives, ascorbic acid, cocoa powder to create chocolate, cocoa butter, palm kernel oil, sunflower lecithin, soy lecithin, and combinations of two or more thereof. Additionally or alternatively, the chewable composition may optionally include cannabidiol (CBD), ginger, pepper, chili, cayenne, turmeric, collagen, butyric acid, salts or esters of beta-hydroxybutyric acid (BHB), ginseng, hyaluronic acid, and a combination of two or more thereof. In some embodiments, the chewable composition can include carrot, apple, blackcurrant, beetroot, pomegranate, and a combination of two or more thereof.

The chewable compositions of the present disclosure may include one or more sweeteners. The chewable composition may include caloric sweeteners and/or non-caloric sweeteners. Examples of non-caloric sweeteners include saccharin, for example, sodium saccharin, acesulfame, neotame, cyclamate or sucralose; natural high-intensity sweeteners, such as thaumatin, stevioside or glycyrrhizin; or sugar alcohols, such as sorbitol, xylitol, maltitol and mannitol. Examples of caloric sweeteners include sugars, such as fructose, glucose, sucrose, and high fructose syrups.

The one or more sweetener(s) may be present in the chewable composition in an amount from about 0.005 to about 60 wt. %, based on the total weight of the chewable composition. For example, when the chewable composition is in the form of a chewable gummy, the chewable composition may have a total amount of the one or more sweetener (s) may be from about 0.005 to about 8 wt. %, about 0.005 to about 6 wt. %, about 0.005 to about 4 wt. %, about 0.005 to about 2 wt. %, about 0.005 to about 1 wt. %, about 0.005 to about 0.5 wt. %, about 0.005 to about 0.1 wt. %; from about 0.01 to about 10 wt. %, about 0.01 to about 8 wt. %, about 0.01 to about 6 wt. %, about 0.01 to about 4 wt. %, about 0.01 to about 2 wt. %, about 0.01 to about 1 wt. %, about 0.01 to about 0.5 wt. %, about 0.01 to about 0.1 wt. %; from about 0.1 to about 10 wt. %, about 0.1 to about 8 wt. %, about 0.1 to about 6 wt. %, about 0.1 to about 4 wt. %, about 0.1 to about 2 wt. %, about 0.1 to about 1 wt. %, about 0.1 to about 0.5 wt. %; from about 0.5 to about 10 wt. %, about 0.5 to about 8 wt. %, about 0.5 to about 6 wt. %, about 0.5 to about 4 wt. %, about 0.5 to about 2 wt. %, about 0.5 to about 1 wt. %; from about 1 to about 10 wt. %, about 1 to about 8 wt. %, about 1 to about 6 wt. %, about 1 to about 4 wt. %, about 1 to about 2 wt. %; from about 2 to about 10 wt. %, about 2 to about 8 wt. %, about 2 to about 6 wt. %, about 2 to about 4 wt. %; from about 3 to about 10 wt. %, about 3 to about 8 wt. %, about 3 to about 6 wt. %, about 3 to about 4 wt. %; from about 4 to about 10 wt. %, about 4 to about 8 wt. %, about 4 to about 6 wt. %; from about 6 to about 10 wt. %, about 6 to about 8 wt. %; from about 8 to about 10 wt. %, including any range or subrange thereof, based on the total weight of the chewable composition. One or more of such sweeteners may be present in the chewable composition in an amount of from about 0.005 to about 5 wt.

% by weight, for example, about 0.01 to about 1 wt. % or about 0.01 to about 0.5 wt. %, by weight of the chewable composition.

The chewable composition may have one or more sweetener(s) present in a higher amount, e.g., when the chewable composition is in the form of a hard and/or brittle chewable composition. For example, the chewable composition may include sweetener(s) in an amount form about 10 to about 50 wt. %, about 10 to about 40 wt. %, about 10 to about 30 wt. %, about 10 to about 25 wt. %, about 10 to about 20 wt. %, about 10 to about 15 wt. %; from about 15 to about 50 wt. %, about 15 to about 40 wt. %, about 15 to about 30 wt. %, about 15 to about 25 wt. %, about 15 to about 20 wt. %; from about 20 to about 50 wt. %, about 20 to about 40 wt. %, about 20 to about 30 wt. %; from about 25 to about 50 wt. %, about 25 to about 40 wt. %, about 25 to about 30 wt. %; from about 30 to about 50 wt. %, about 30 to about 40 wt. %; from about 35 to about 50 wt. %, about 35 to about 40 wt. %; from about 40 to about 50 wt. %, including ranges and subranges thereof, based on the total weight of the chewable composition.

In some embodiments, the chewable composition preferably is substantially free or free of caloric sweeteners. For example, the chewable compositions may have about 4 wt. % or less, about 3 wt. % or less, about 2 wt. % or less, about 1 wt. % or less, about 0.5 wt. % or less, or about 0.1 wt. % or less, based on the weight of the chewable composition. In at least one embodiment, the chewable composition contains about 0 wt. % or 0 wt. % of caloric sweeteners, based on the weight of the chewable composition.

The chewable compositions of the present disclosure may include a flavoring agent. Suitable flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Additional flavorants may include, but are not limited to menthol, artificial vanilla, cinnamon derivatives, and various fruit flavors, spearmint oil, peppermint oil, cinnamon oil, oil of wintergreen (methylsalicylate), clove oil, bay oil, anise oil, eucalyptus oil, thyme oil, cedar leaf oil, oil of nutmeg, oil of sage, oil of bitter almonds, cassia oil, and a combination of two or more thereof. The flavorants can include artificial, natural or synthetic fruit flavors such as citrus or fruit oils and/or essences including apple, apricot, banana, blueberry, cherry, grape, grapefruit, kiwi, lemon, lime, orange, pear, peach, pineapple, plum, raspberry, strawberry, tangerine, watermelon, and a combination of two or more thereof. Flavorings can also include, for example, aldehydes and esters including cinnamyl acetate, cinnamaldehyde, citral diethylacetal, dihydrocarvyl acetate, eugenyl formate, p-methylamisol, acetaldehyde (apple); benzaldehyde (cherry, almond), anisic aldehyde (licorice, anise); cinnamic aldehyde (cinnamon); citral, e.g., alpha citral (lemon, lime); ethyl vanillin (vanilla, cream); hellotropine, i.e., piperonal (vanilla, cream); vanillin (vanilla, cream); alpha-amyl cinnamaldehyde (spicy fruity flavors); butyraldehyde (butter, cheese); valcraldehyde (butter, cheese); citronellal; decannal (citrus fruits); aldehyde C-8 (citrus fruits); aldehyde C-9 (citrus fruits); aldehyde C-12 (citrus fruits); 2-ethylbutyraldehyde (berry fruits); tolyl aldehyde (cherry, almond); veratraldehyde (vanilla); 2,6-dimethyl-5-heptenal, i.e., melonal (melon); 2,6-dimethyloctanal (green fruit); and 2-dodecenal (citrus, mandarin), mixtures thereof and the like. Additional flavor compounds include ethylacetate, thiophene, ethylpropionate, ethyl butyrate, 2-hexanoate, 2-methylpyazine, heptaldehyde, 2-octanone, limonene, and eugenol.

The flavoring agent is typically incorporated in the chewable composition at a concentration of about 0.01 to about 3 wt. % by weight of the chewable composition. For example, the amount of flavorant(s) present in the chewable composition may be from about 0.01 to about 2 wt. %, about 0.01 to about 1 wt. %, about 0.01 to about 0.5 wt. %, about 0.01 to about 0.1 wt. %; from about 0.1 to about 3 wt. %, about 0.1 to about 2 wt. %, about 0.1 to about 1 wt. %, about 0.1 to about 0.5 wt. %; from about 0.5 to about 3 wt. %, about 0.5 to about 2 wt. %, about 0.5 to about 1 wt. %; from about 1 to about 3 wt. %, about 1 to about 2 wt. %; from about 2 to about 3 wt. %, including any range or subrange thereof, based on the total weight of the chewable composition.

The chewable composition (e.g., oral care composition) of the disclosure may include one or more pigments, such as whitening pigments, and/or colorants. In some embodiments, the whitening pigments include particles ranging in size from about 0.1 μm to about 10 μm with a refractive index greater than about 1.2. Suitable whitening agents include, without limitation, titanium dioxide particles, zinc oxide particles, aluminum oxide particles, tin oxide particles, calcium oxide particles, magnesium oxide particles, barium oxide particles, silica particles, zirconium silicate particles, mica particles, talc particles, tetracalcium phosphate particles, amorphous calcium phosphate particles, alpha-tricalcium phosphate particles, beta-tricalcium phosphate particles, hydroxyapatite particles, calcium carbonate particles, zinc phosphate particles, silicon dioxide particles, zirconium silicate particles, or the like, or mixtures and combinations thereof. The whitening pigment, such as titanium dioxide particles, may be present in an amount that is sufficient to whiten the teeth.

Exemplary colorants can include natural or uncertified colors from natural sources or certified colors for the effect of color. In some embodiments, the colorant can include dyes, certified aluminum lakes or colors derived from a natural source. The colorant may be water-based, oil-based or dry. The colorants can be primary colors, blends of colors or discrete mixtures of colors, such as confetti. The concentrations of the colorant in the chewable composition may be from trace amount to about 0.6 wt. %, from about 0.1 to about 0.5 wt. %, about 0.2 to about 0.4 wt. %, or about 0.15 to about 0.35 wt. %, based on the total weight of the chewable composition.

EXAMPLES

Example 1—Effect of Formulations Containing Arginine

The production of acids by acidogenic oral bacteria leads to the demineralization of tooth enamel and eventually dental caries. Catabolism of arginine via the arginine deiminase pathway by beneficial oral commensals produces ammonia, which aids in the neutralization of plaque acids and the prevention of tooth decay. An in vitro planktonic ammonia assay is performed to confirm arginine's availability and ammonia production for several test compositions.

Several chewable compositions containing arginine are created as described in Table 1 below. The amount of each ingredient in Compositions 1-4 was the same when such ingredient was included in the respective Compositions. For instance, the amount of pectin included in Compositions 1-4 was the same. The amount of arginine included in both Compositions 2 and 4 was 0.4 wt. %, based on the total weight of the chewable compositions. The amount of xylitol included in Compositions 2-4 was 10 wt. %, based on the total weight of the chewable compositions. The amount of dicalcium phosphate dihydrate included in Compositions 2-4 was 10 wt. %, based on the total weight of the chewable compositions.

TABLE 1

| Test Formulation | Ingredients |
|---|---|
| Composition 1 | Pectin |
| Composition 2 | Pectin + Arginine + Xylitol + Dicalcium Phosphate dihydrate + vitamins D3 and B12 |
| Composition 3 | Pectin + Xylitol + Dicalcium Phosphate dihydrate + vitamins D3 and B12 |
| Composition 4 | Pectin + Arginine + Xylitol + Dicalcium Phosphate dihydrate |

Further comparator compositions in the form of toothpastes are created as defined below in Table 2.

TABLE 2

| Comparator Formulation | Ingredients |
|---|---|
| Composition 5 | 1,450 ppm Fluoride + calcium carbonate base (12.5% slurry) |
| Composition 6 | 1.5% Arginine + 1,450 ppm Fluoride + calcium carbonate base (12.5% slurry) |

Two-way ANOVA with treatment as factor is conducted to determine whether significant differences existed between treatments. The treatment effect is considered significant if the p value was <0.05 (95% confidence level). If a significant difference was detected, a Tukey's multiple comparison test is used to assess pairwise differences among the treatments.

Basal levels of ADS activity (ammonia production) are quantified in the negative control (Composition 5) which contains no arginine, as well as in the two arginine-free gummies. Ammonia production measured on samples treated with the positive control toothpaste (Composition 6) and the experimental gummies, all containing arginine, is not statistically different. Treatment of *S. gordonii* suspensions with arginine-containing samples (Composition 2 and Composition 4) results in approximately 8× more ammonia generation compared to the no arginine controls. Removal of vitamins $D_3$ and $B_{12}$ is not detrimental to arginine degradation which suggests these vitamins impact ammonia generation. This data is summarized below in Table 3.

TABLE 3

| Formulation | Ammonia (nmol/ul) (Mean ± StDev) | Grouping |
|---|---|---|
| Composition 2 | 0.350961 ± 0.0284 | A |
| Composition 6 | 0.341261 ± 0.01053 | A |
| Composition 4 | 0.328451 ± 0.00781 | A |
| Composition 3 | 0.057335 ± 0.00562 | B |
| Composition 1 | 0.036322 ± 0.00149 | B |
| Composition 5 | 0.033067 ± 0.00236 | B |

*Means that do not share a letter are significantly different.

Arginine degradation via the arginine deiminase pathway and the resulting production of ammonia is a natural defense mechanism against dental caries. Presence of ammonia upon treatment with this new nutritional gummy containing arginine confirms the active catabolism of arginine by an orally derived microorganism. These results suggest ingestion of this nutritional gummy containing arginine could lead to a healthier mouth pH via ammonia production and sugar acids neutralization.

Example 2—Preparation of Oral Care Compositions

Non-limiting, exemplary oral care compositions were prepared in accordance with aspects of the invention. Example Compositions A-F (Exs. A-F) were chewable compositions in the form of gummies. Comparative Composition 1 contained water and served as a control. Comparative Compositions 2-4 (Comps. 2-4) were in the form of gummies. The formulation for Exs. A-F and Comps. 1-4 are shown in Table 4, below.

TABLE 4

|  | Ex. A (wt. %) | Ex. B (wt. %) | Ex. C (wt. %) | Ex. D (wt. %) | Ex. E (wt. %) | Ex. F (wt. %) | Compar. Comp. 1 (wt. %) | Compar. Comp. 2 (wt. %) | Compar. Comp. 3 (wt. %) | Compar. Comp. 4 (wt. %) |
|---|---|---|---|---|---|---|---|---|---|---|
| Arginine | 0.5 | 5 | 0.5 | 5 | 0.5 | 5 | 0 | 0 | 0 | 0 |
| Gelatin | ~10-20 | ~10-20 | 0 | 0 | 0 | 0 | 0 | ~10-20 | 0 | 0 |
| Carrageenan | 0 | 0 | ~10-20 | ~10-20 | 0 | 0 | 0 | 0 | ~10-20 | 0 |
| Pectin | 0 | 0 | 0 | 0 | 10 | 10 | 0 | 0 | 0 | 10 |
| Water | ~33.2 | ~31.6 | ~57.6 | ~53.1 | 74.5 | 70 | 100 | ~33.2 | ~58.1 | 75 |

Example 3—Evaluation of Oral Care Compositions of Example 2

The oral care compositions from Example 2 were evaluated to assess the potential ability to preempt plaque acids and reduce and/or prevent tooth decay. In vitro planktonic ammonia assays were performed for Exs. A-F and Comps. 1-4 to determine the amount of ammonia production associated with such chewable compositions. Specifically, an overnight culture of *Streptococcus gordonii* (arginolytic oral microorganism) was thoroughly rinsed and resuspended in phosphate buffer. These bacterial suspensions (normalized by cell weight) were incubated at a temperature of 37° C. in the presence of sucrose, dentifrice, and gummy slurries. Following incubation, the suspensions were centrifuged and the supernatants were used to quantify ammonia generation via a commercially available assay in which ammonia reacts with phenol in the presence of hypochlorite to form indophenol, a product quantifiable by spectrophotometry at 670 nm. FIGURE shows the results of the ammonia assays.

Example 4—Evaluation of the Chewiness of the Oral Care Compositions

Chewable compositions were prepared according to similar procedures as the chewable compositions of Examples 1 and 2. The chewable compositions were prepared to have the formulations of Example Compositions A-D, which are reproduced below in Table 5.

TABLE 5

|  | Ex. A (wt. %) | Ex. B (wt. %) | Ex. C (wt. %) | Ex. D (wt. %) |
| --- | --- | --- | --- | --- |
| Arginine | 0.5 | 5 | 0.5 | 5 |
| Gelatin | ~10-20 | ~10-20 | 0 | 0 |
| Carrageenan | 0 | 0 | ~10-20 | ~10-20 |
| Water | ~33.2 | ~31.6 | ~57.6 | ~53.1 |

Two commercially available chewable gummies (Comparative Compositions 5 and 6) were evaluated as comparative compositions. The chewiness of the Example Compositions A-D and Comparative Compositions 5 and 6 were evaluated by assessing their hardness. Specifically, the hardness of each chewable composition was assessed by compressing each chewable composition to a strain of 10% and to a strain of about 50%. The compression probe used for assessing the hardness of the chewable compositions had a trigger force of 8 grams, a descending speed before contact of 10 mm/sec, a descending speed during contact of 1 mm/sec, and a posttest recover speed of 10 mm/sec. The force at 10% strain was recorded as the peak force at 10% strain and the force at about 50% strain was recorded as the peak force at 50% strain.

Figure 2:
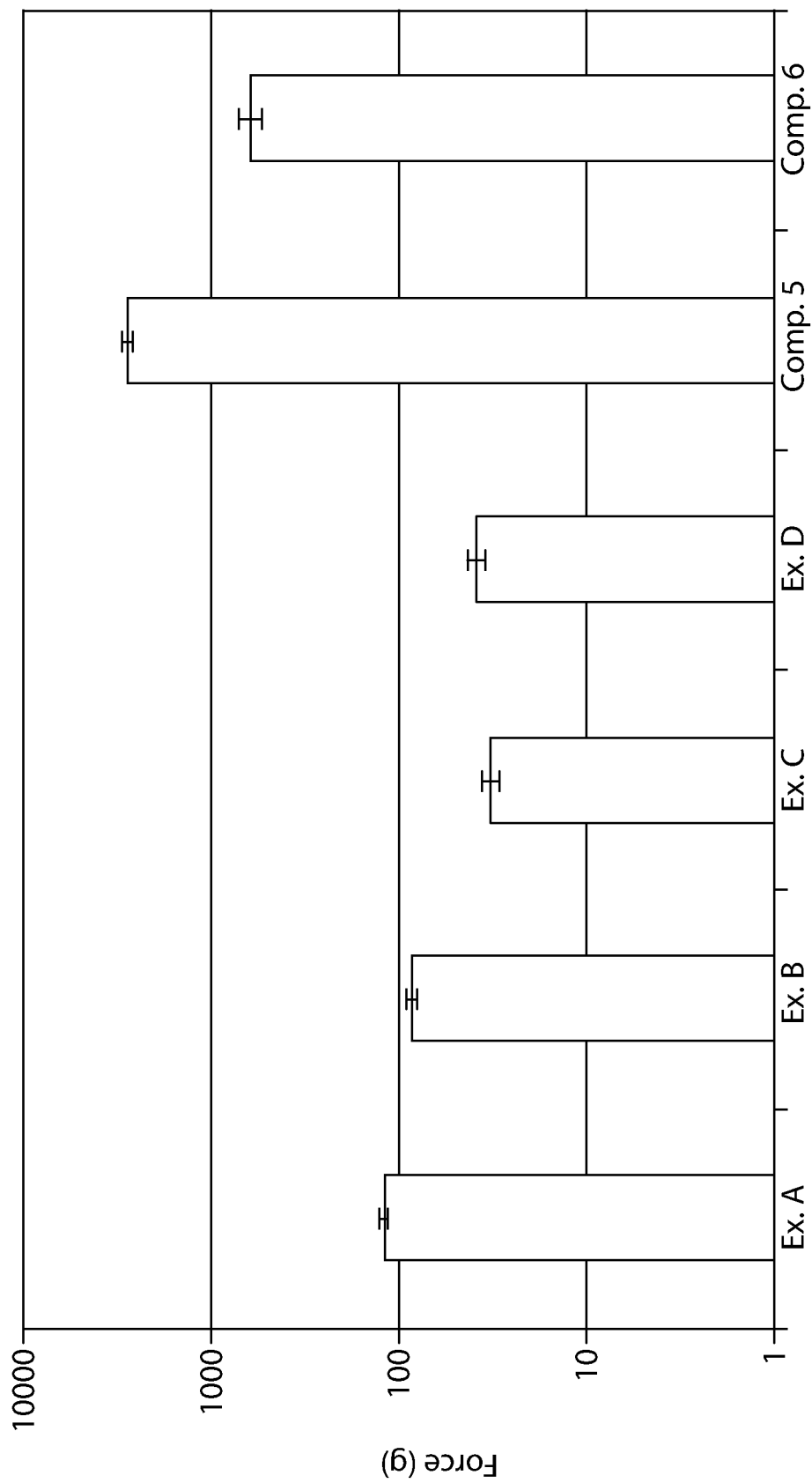
FIG. 2 is a bar graph of the peak force at 10% strain for example chewable compositions and comparative chewable compositions according to aspects of the invention.
Figure 3:
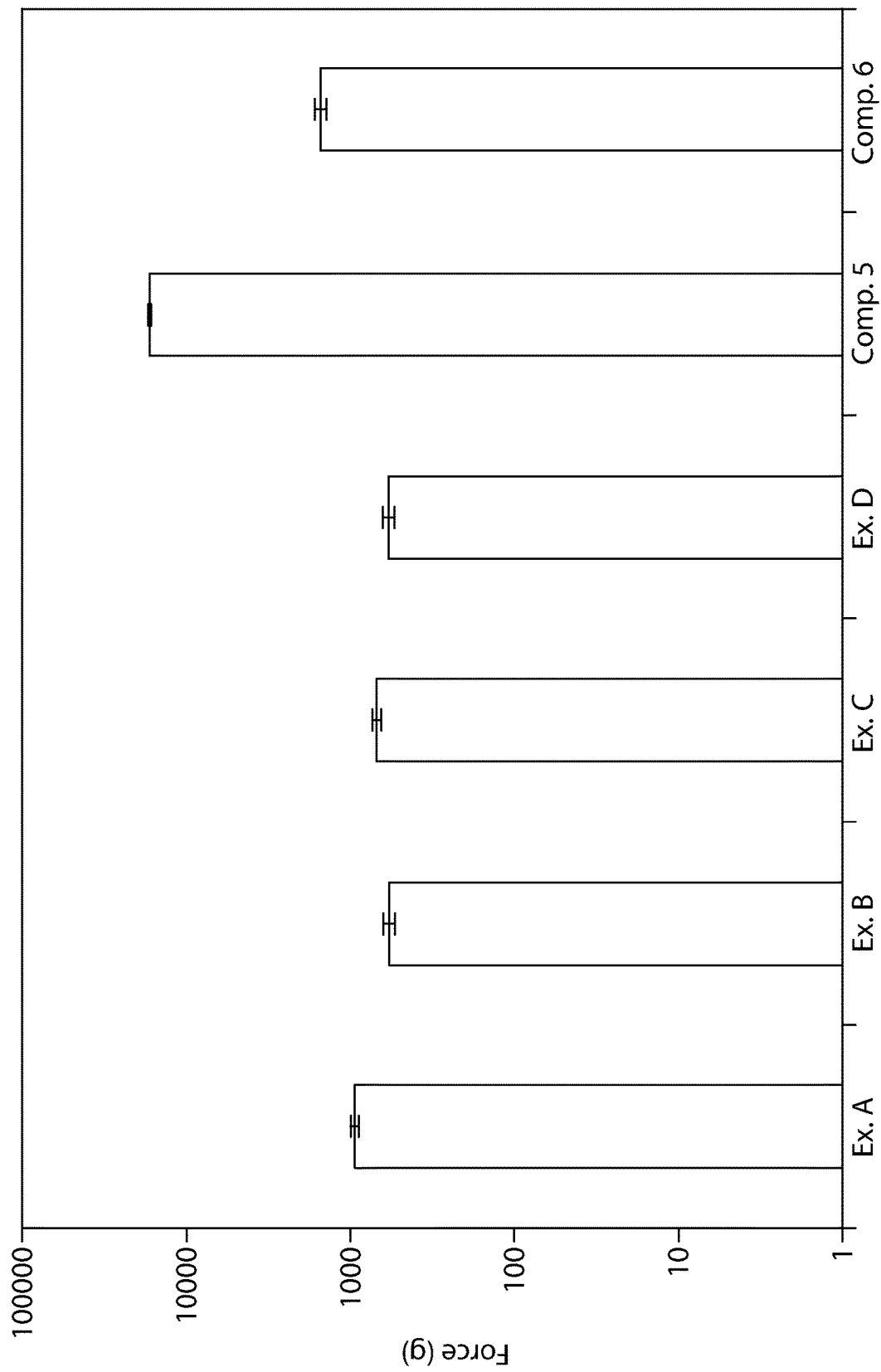
FIG. 3 is a bar graph of the peak force at 50% strain for example chewable compositions and comparative chewable compositions according to aspects of the invention.
Figure 4:
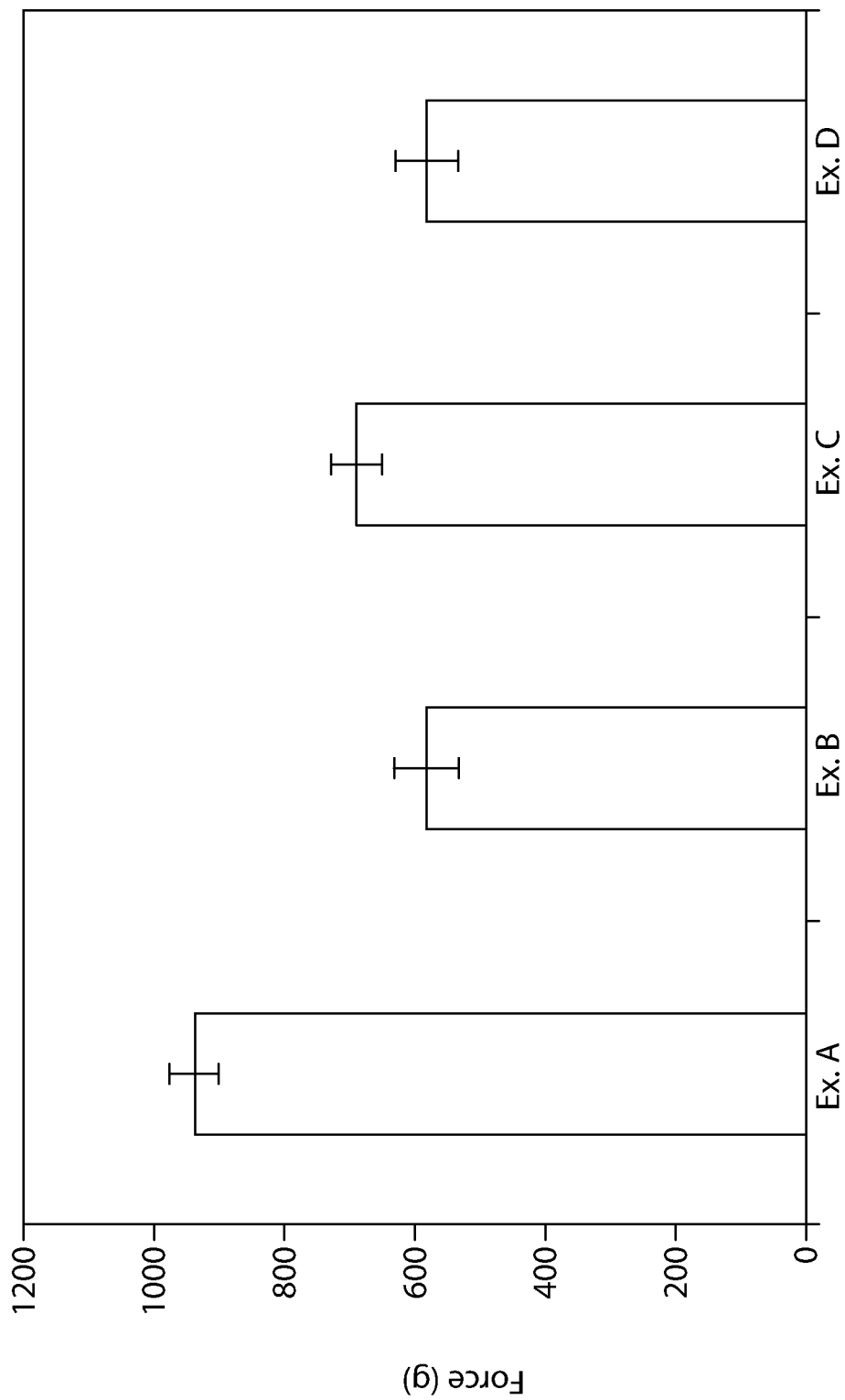
FIG. 4 is a bar graph of the peak force at 50% strain for example chewable compositions of FIG. 3.

The peak force at 10% strain for Example Compositions A-D and Comparative Compositions 5 and 6 is presented in FIG. 2. The peak force at 50% strain for Example Compositions A-D and Comparative Compositions 5 and 6 is presented in FIG. 3. FIG. 4 shows the peak force at 50% strain for Example Compositions A-D.

While the disclosure has been described with respect to specific examples including presently preferred modes of carrying out the disclosure, those skilled in the art will appreciate that there are numerous variations and permutations of the systems and techniques described above. It is to be understood that other embodiments may be utilized and structural and functional modifications may be made without departing from the scope of the present disclosure. Thus, the scope of the disclosure should be construed broadly as set forth in the appended claims.

What is claimed is:

1. A chewable composition comprising:
   from about 1 to about 20 wt. % of a gelling agent consisting of carrageenan;
   from about 0.01 to about 20 wt. % of arginine and or a salt thereof, wherein the weight ratio of carrageenan to arginine and or salt thereof, is from about 10:1 to about 1:1;
   from about 20 to about 60 wt. % of water; and
   a sweetener,
   wherein all weight percentages are based on the total weight of the chewable composition.

2. The chewable composition according to claim 1, further comprising from about 0.5 to about 20 wt. % of a source of calcium comprising calcium carbonate, calcium bicarbonate, calcium phosphate, calcium sulfate, or a combination of two or more thereof.

3. The chewable composition according to claim 1 further comprising a gelling agent comprising alginate, pectin, gellan, gelatin, agar, modified starch, methyl cellulose, hydroxypropylmethyl cellulose, xanthan gum, gum tracaganth, or a combination of two or more thereof.

4. The chewable composition according to claim 1, wherein the weight ratio of gelling agent to arginine and or salt thereof, is from about 6:1 to about 1:1.

5. The chewable composition according to claim 1, wherein the sweetener is present in an amount from about 0.005 to about 60 wt. %; optionally, about 0.005 to about 8 wt. %, about 0.005 to about 6 wt. %, about 0.005 to about 4 wt. %, about 0.1 to about 8 wt. %, about 0.1 to about 6 wt. %, about 0.1 to about 4 wt. %, about 0.5 to about 8 wt. %, about 0.5 to about 6 wt. %, about 0.5 to about 4 wt. %, about 1 to about 8 wt. %, about 1 to about 6 wt. %, or about 1 to about 4 wt. %.

6. The chewable composition according to claim 1, wherein the sweetener is a non-caloric sweetener selected from saccharin, natural high-intensity sweeteners, sugar alcohols, and a combination of two or more thereof.

7. The chewable composition according to claim 1, further comprising a mineral and/or vitamin selected from vitamin A, vitamin C, vitamin D, vitamin E, vitamin K, vitamin B6, vitamin $D_3$, vitamin $B_{12}$, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and a combination of two or more thereof.

8. The chewable composition according to claim 1, further comprising from about 0.01 to about 2 wt. % of a flavorant comprising one or more fruit oils and/or essence selected from apple, apricot, banana, blueberry, cherry, grape, grapefruit, kiwi, lemon, lime, orange, pear, peach, pineapple, plum, raspberry, strawberry, tangerine, watermelon, and a combination of two or more thereof.

9. The chewable composition according to claim 1, wherein the chewable composition is in the form of a gummy.

10. The chewable composition according to claim 1, wherein the chewable composition is an edible composition.

11. A chewable composition comprising:
   from about 5 to about 20 wt. % of a gelling agent selected from the group consisting of pectin, carrageenan, and a combination thereof;

from about 0.01 to about 20 wt. % of one or more amino acid and/or a salt thereof comprising arginine and/or a salt thereof;
a sugar alcohol;
from about 20 to about 60 wt. % of water;
optionally, a source of calcium,
wherein all weight percentages are based on the total weight of the chewable composition.

12. An oral composition consisting of:
arginine and or salts thereof; and
a gelling agent selected from pectin, carrageenan, and a combination thereof;
a sugar alcohol;
from about 20 to about 60 wt. % of water;
optionally, a source of calcium; and
optionally, a vitamin and/or mineral,
wherein the oral composition has a peak force of from about 50 to about 150 grams at a 10% strain.

13. The oral composition according to claim 12, wherein the oral composition has a peak force of from about 400 to about 1100 grams at a 50% strain.

14. The oral composition according to claim 12, wherein the oral composition has a resilience value of from about 5% to about 65%.

15. The oral composition according to claim 12, wherein the oral composition is not permanently deformed by a peak force of less than about 1100 grams at a 50% strain.

16. The oral composition according to claim 12, wherein the oral composition is permanently deformed by a peak force of greater than about 1100 grams at a 50% strain.

17. The oral composition according to claim 12, wherein the oral composition is dry to the touch.

18. The oral composition according to claim 12, in the form of a gummy.

19. The chewable composition according to claim 11, wherein the weight ratio of gelling agent to amino acid or salt thereof, is from about 25:1 to about 1:1.

* * * * *